(12) United States Patent
Powell et al.

(10) Patent No.: US 7,867,181 B2
(45) Date of Patent: Jan. 11, 2011

(54) NECK SUPPORT

(76) Inventors: Marcus W. Powell, 2893 Quaker Ave., New London, IA (US) 52645; Jesse G. Asper, II, 13723 Lurgan Rd, Newburg, PA (US) 17240; Tim Keldgord, Jr., 400 East McKinley St., Mt. Pleasant, IA (US) 52641

( * ) Notice: Subject to any disclaimer, the term of this patent is extended or adjusted under 35 U.S.C. 154(b) by 0 days.

(21) Appl. No.: 12/101,492

(22) Filed: Apr. 11, 2008

(65) Prior Publication Data
US 2009/0204041 A1    Aug. 13, 2009

Related U.S. Application Data

(63) Continuation-in-part of application No. 12/030,325, filed on Feb. 13, 2008.

(51) Int. Cl.
*A61F 5/00* (2006.01)
*A47B 7/00* (2006.01)
*A47C 20/00* (2006.01)

(52) U.S. Cl. .................. 602/18; 5/622; 5/636

(58) Field of Classification Search .......... 602/13, 602/17, 18, 19, 32, 34, 35, 36; 441/118, 441/119, 123, 124; 2/410, 6.1, 6.2; 5/644, 5/708, 622, 603, 636, 637; 297/397; 128/DIG. 23, 128/DIG. 20
See application file for complete search history.

(56) References Cited

U.S. PATENT DOCUMENTS

| | | | |
|---|---|---|---|
| 5,181,279 A | 1/1993 | Ross | |
| 5,363,524 A * | 11/1994 | Lang | 5/640 |
| 5,402,535 A | 4/1995 | Green | |
| 6,125,478 A | 10/2000 | Alaloof | |
| 6,622,325 B1 * | 9/2003 | Garza | 5/636 |
| 6,637,059 B1 | 10/2003 | Baker | |
| 6,745,418 B1 * | 6/2004 | Turner, Jr. | 5/638 |
| 7,017,195 B2 | 3/2006 | Buckman et al. | |
| 7,089,602 B2 | 8/2006 | Talluri | |
| 7,150,048 B2 | 12/2006 | Buckman | |
| 2003/0139695 A1 * | 7/2003 | Riach | 602/13 |
| 2003/0158015 A1 * | 8/2003 | Watson | 482/10 |

* cited by examiner

*Primary Examiner*—Patricia M Bianco
*Assistant Examiner*—Ophelia Hawthorne

(57) ABSTRACT

A neck support/brace for protecting a neck has a flexible collar with a top wall, bottom wall, sidewalls and sectional walls disposed therebetween that form compartments therein. A plurality of cells are disposed within the compartment. Each of the fluid cells have a valve element disposed therein. When the pressure acting upon the cells is below a threshold pressure, fluid or air flows through the valve element to allow movement of the neck. Alternatively when the pressure on the cells is above the threshold pressure the valve element closes preventing fluid or air flow out of the fluid cell thus causing the cell to stay inflated and provide resistance to a neck movement.

19 Claims, 8 Drawing Sheets

NECK SUPPORT

CROSS REFERENCE TO A RELATED APPLICATION

This application is a continuation-in-part of U.S. Ser. No. 12/030,325 filed Feb. 13, 2008.

BACKGROUND OF THE INVENTION

This invention relates a neck support collar. More specifically this invention relates to a neck support collar that allows for neck movement while still protecting the neck under pressure.

Neck supports/braces for athletic and similar activities are well known in the art. Typically, these braces are of a solid construction that, while providing neck support, limit a user's range of motion and are uncomfortable to wear. Other braces, that provide greater comfort, do not provide sufficient support to prevent injuries in the presence of a sudden impact. In addition, current neck braces are not designed to break away in the presence of extreme force. Therefore, a need exists in the art for a neck support that addresses these deficiencies.

An objective of the invention is to provide a neck support that allows for neck movement under normal conditions and support when greater force loads are incurred.

These and other objectives, features, or advantages of the present invention will become apparent from the specification and claims.

SUMMARY OF THE INVENTION

A neck support/brace for protecting a neck has a flexible collar with a top wall, bottom wall, sidewalls and sectional walls disposed therebetween that form compartments therein. A plurality of cells are disposed within the compartment. Each of the fluid cells have a valve element disposed therein. When the pressure acting upon the cells is below a threshold pressure, fluid or air flows through the valve element to allow movement of the neck. Alternatively when the pressure on the cells is above the threshold pressure the valve element closes preventing fluid or air flow out of the fluid cell thus causing the cell to stay inflated and provide resistance to a neck movement.

DETAILED DESCRIPTION OF THE PREFERRED EMBODIMENT OF THE INVENTION

Figure 1:
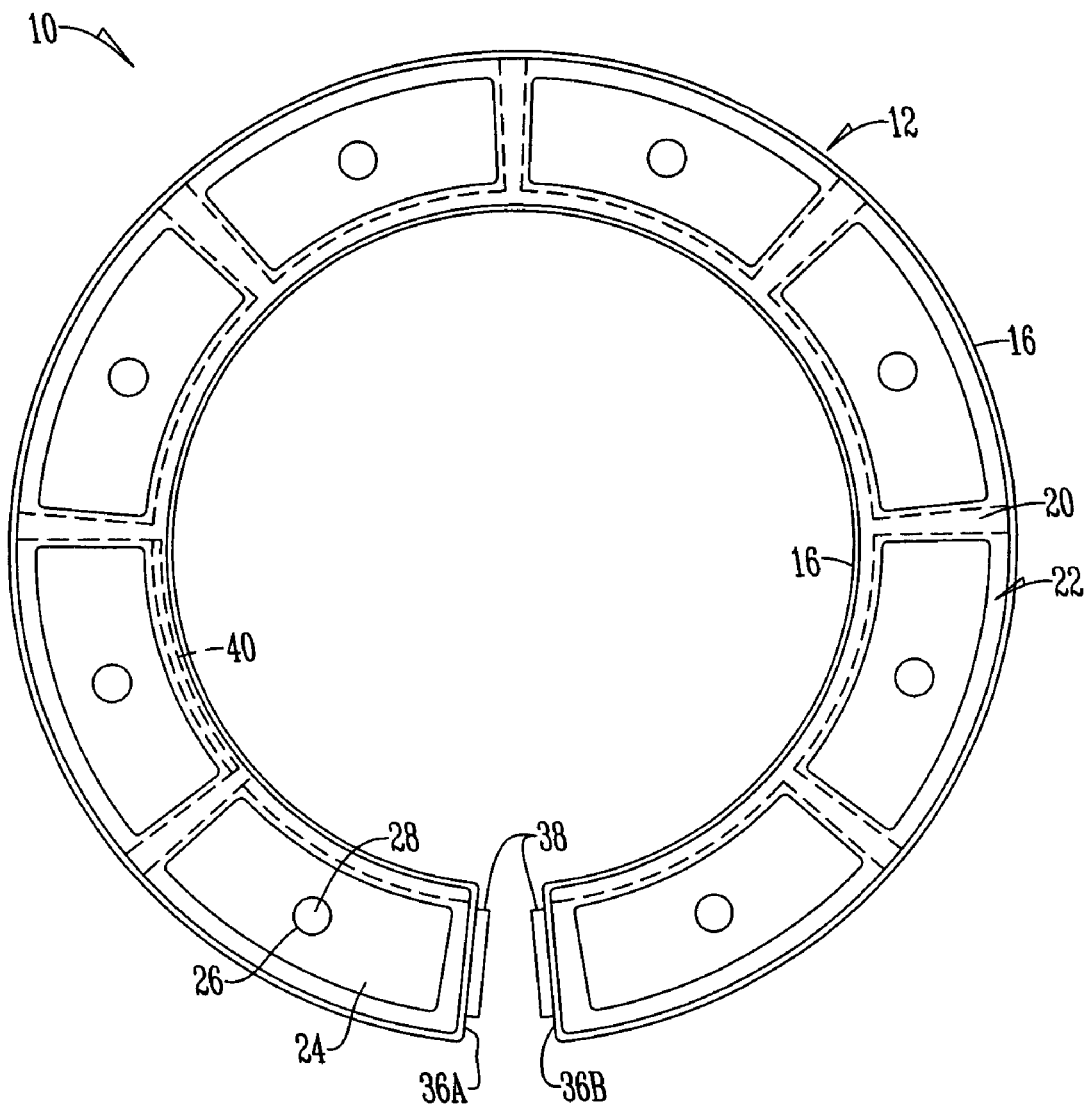
FIG. 1 is a plan view of a neck support.
Figure 2:
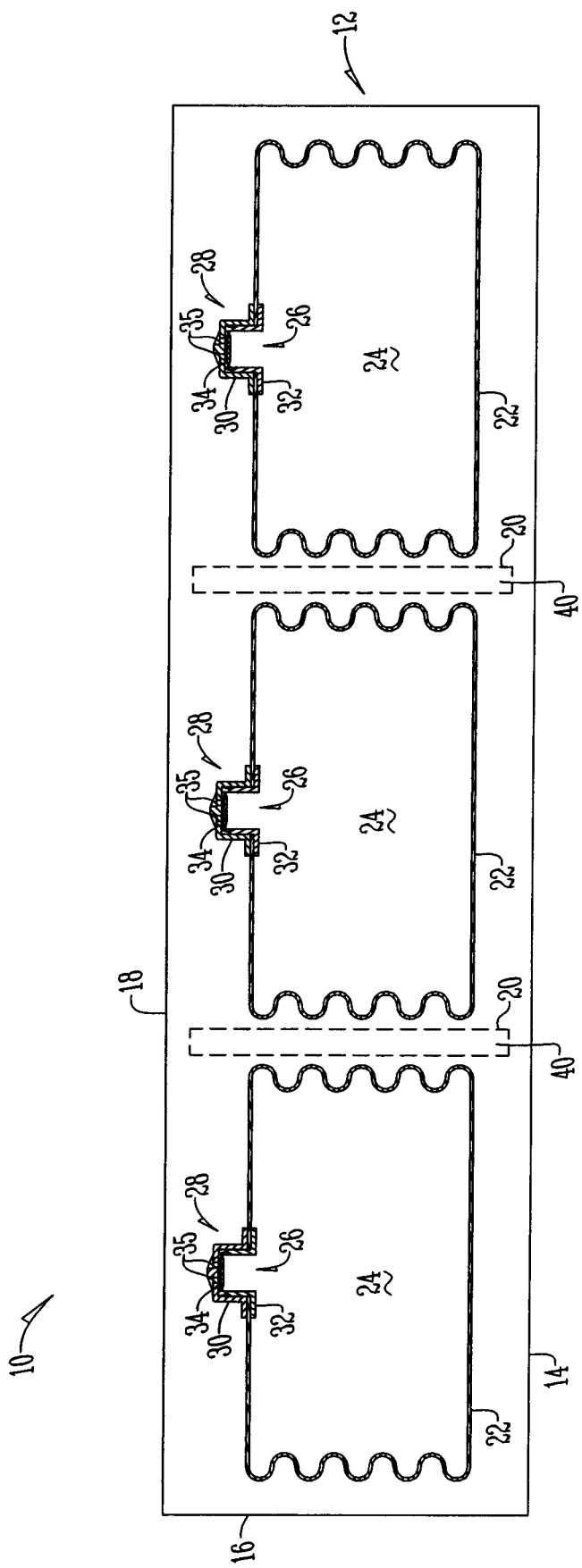
FIG. 2 is a side view of a neck support.
Figure 3:
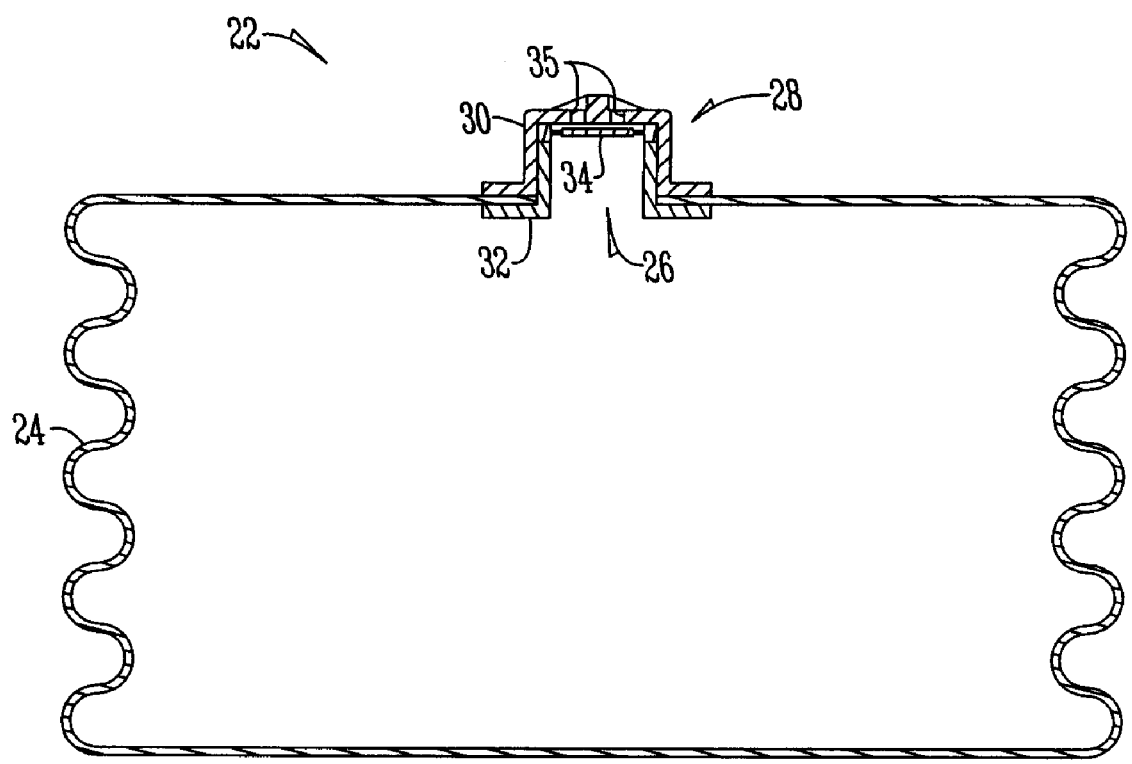
FIG. 3 is a side view of a preferred valve element.
Figure 4:
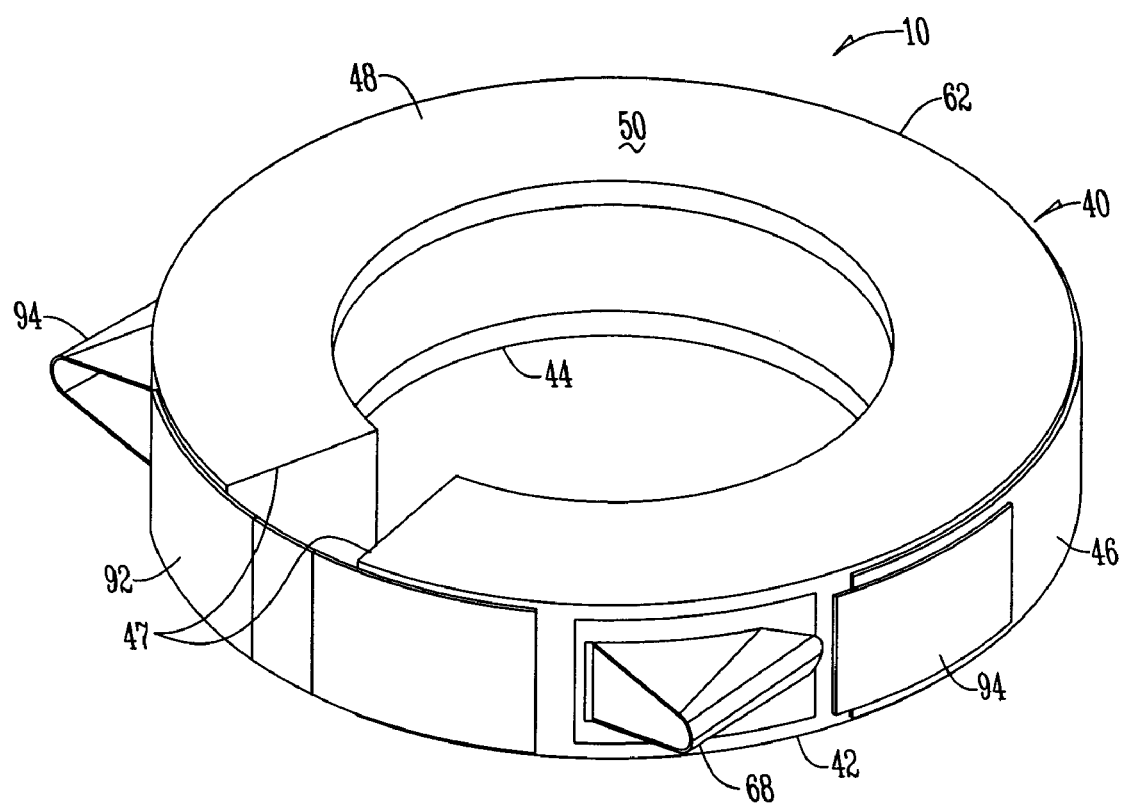
FIG. 4 is a perspective view of a neck support.
Figure 5:
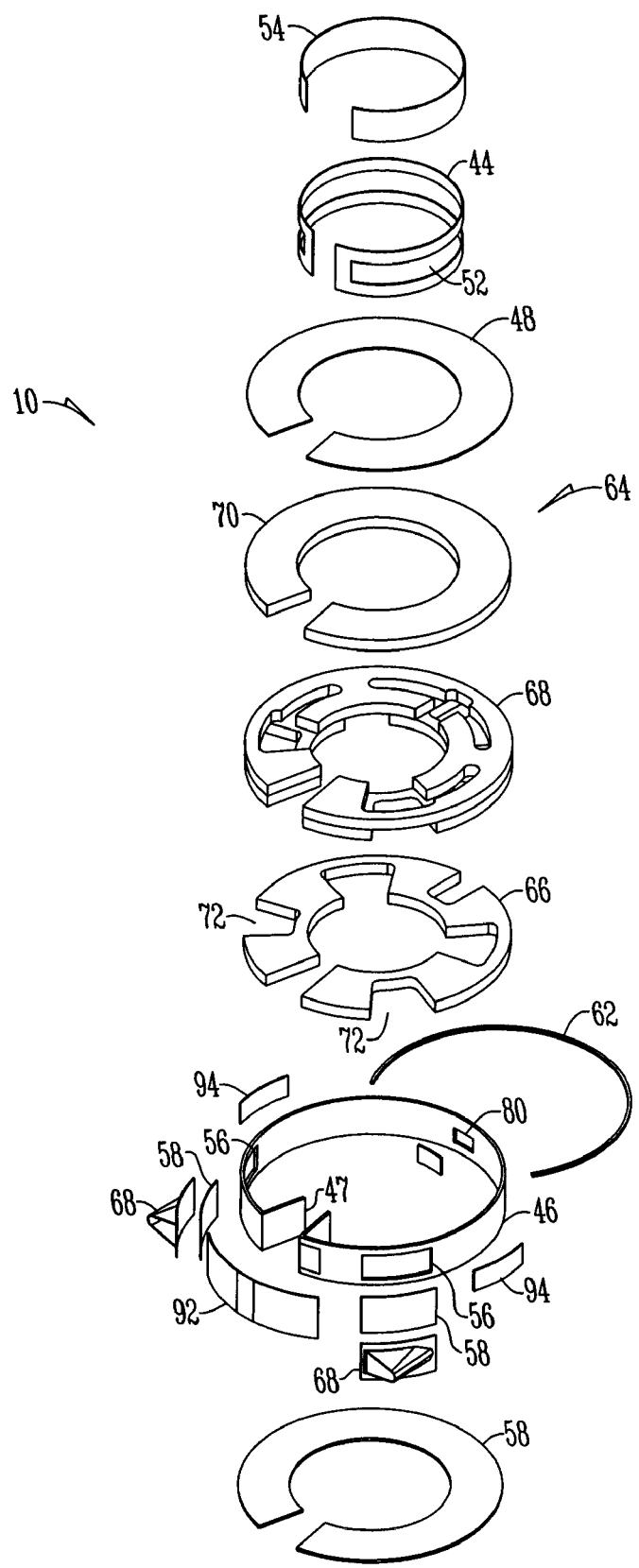
FIG. 5 is an exploded view of a neck support.
Figure 6:
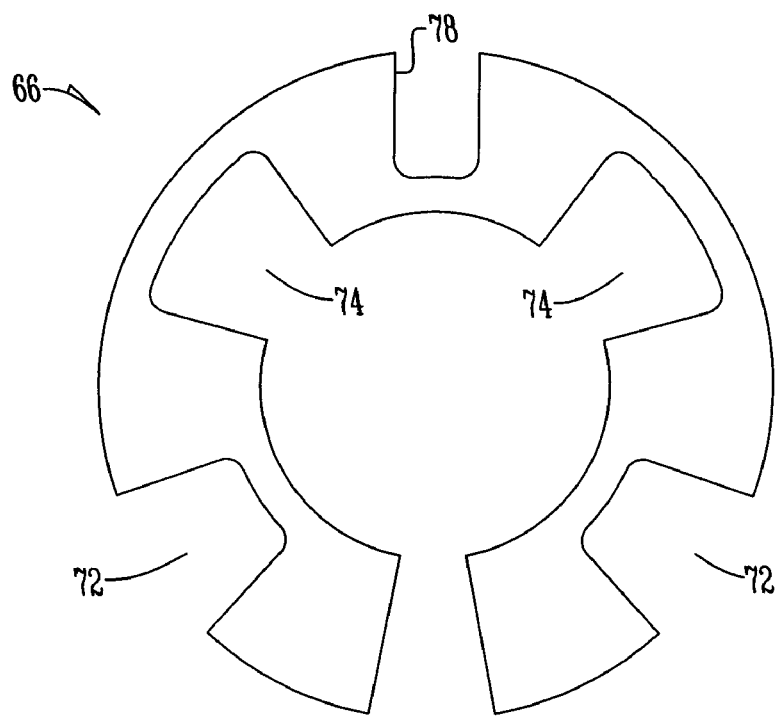
FIG. 6 is a top view of a section of a support member.
Figure 7:
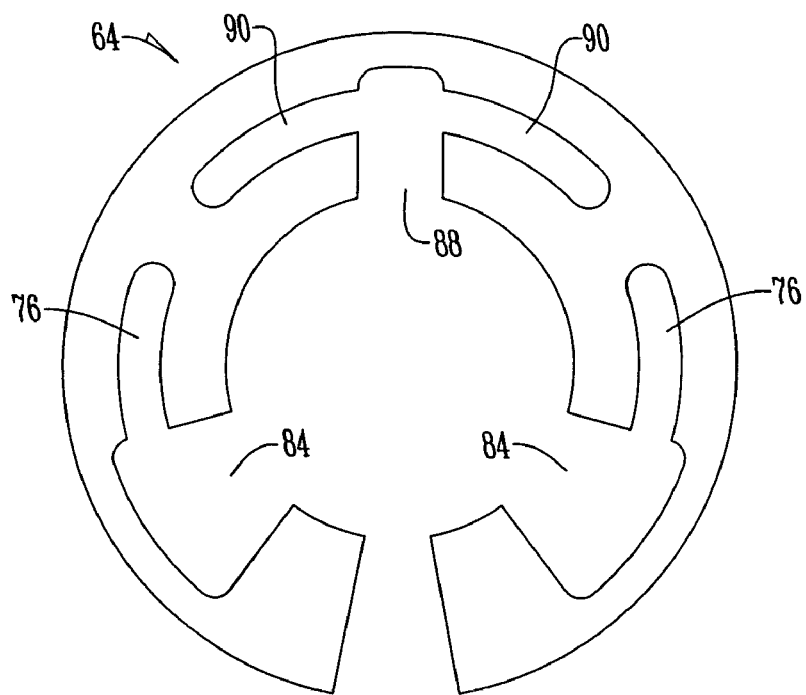
FIG. 7 is a top view of a section of a support member.
Figure 8:
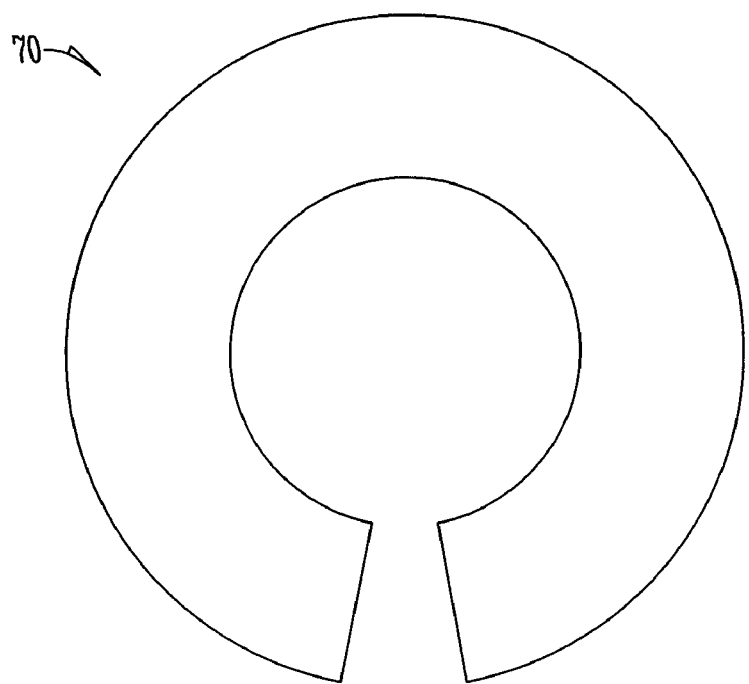
FIG. 8 is a top view of a section of a support member.
Figure 9:
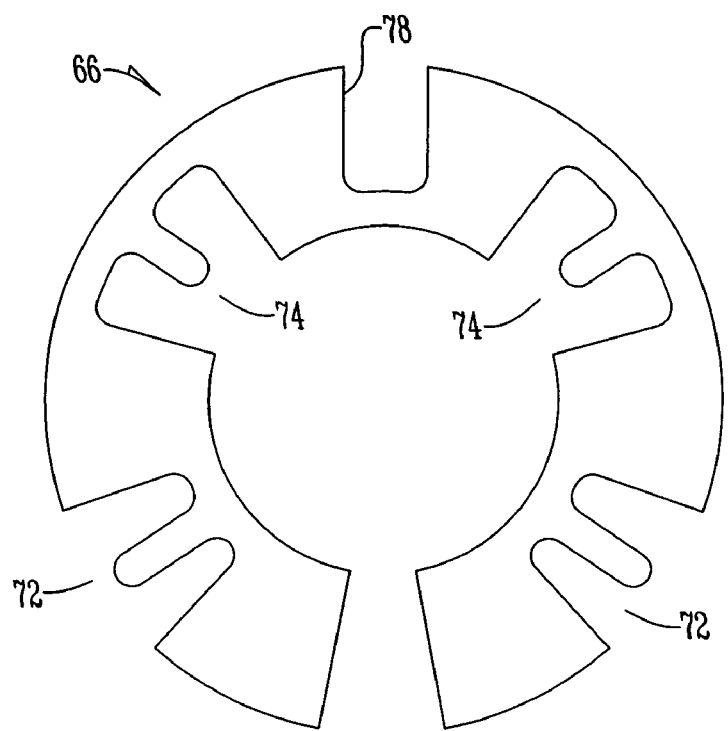
FIG. 9 is a top view of a section of a support member.
Figure 10:
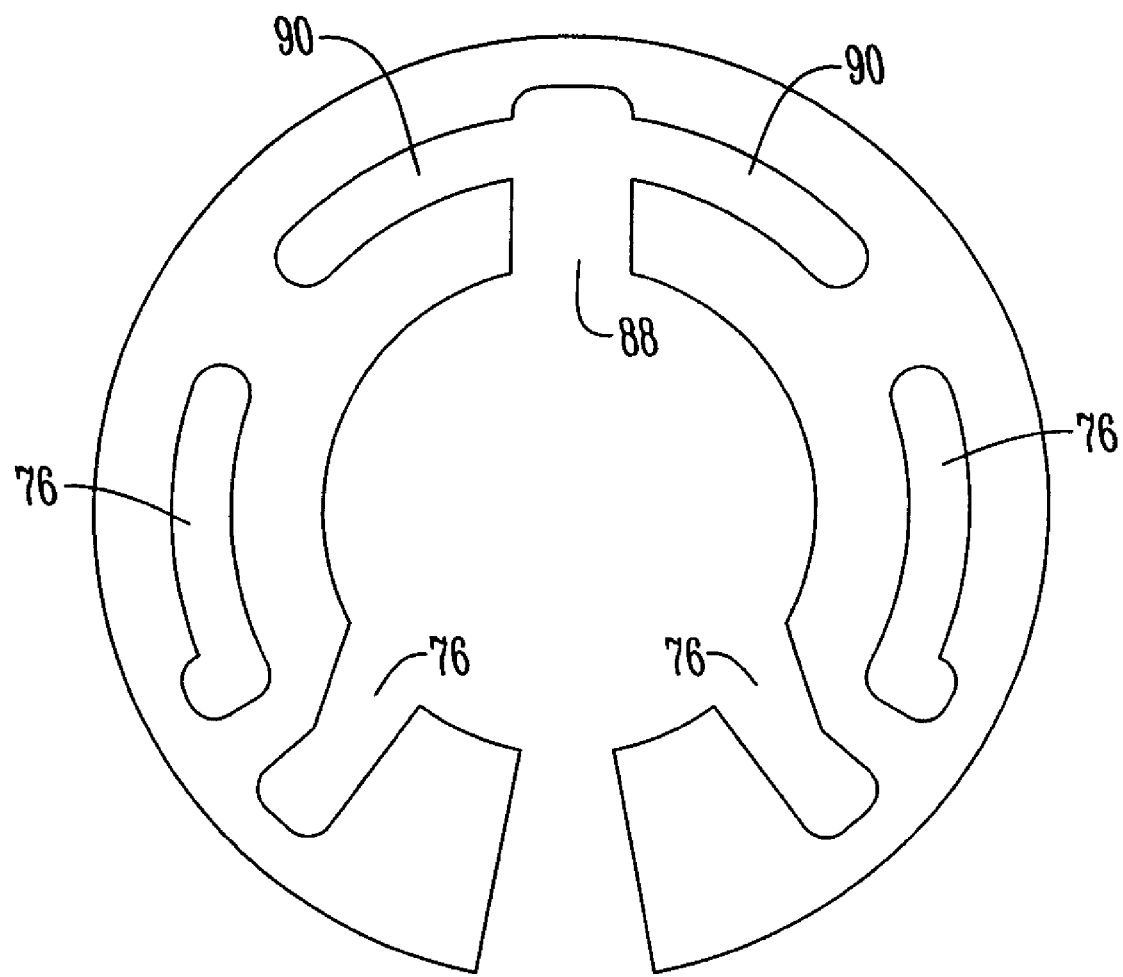
FIG. 10 is a top view of a section of a support member.

Referring to the figures, a neck support is shown by reference numeral 10. While a neck support is shown, by example only, the invention may be adapted for use with a helmet, chest protector, knee support, or the like.

The neck support 10 has a collar 12 having a bottom 14, sidewalls 16, and a removable top wall 18. Sectional walls 20 extend between the sidewalls 16 to form a compartment 22 that snugly receives a cell 24. The cell 24 is made of an elastomer and is of any shape or size. Each cell 24 has a port 26 with a check valve 28 disposed within the port 26.

The check valve 28 is of any type, structure and shape, but preferably has an outer body 30, an inner body 32, and a diaphragm 34 disposed therebetween that is capable of sealing an opening 35 in the inner and outer body. In addition, the check valve 28 preferably permits the release of air from the cell 24 when force is applied below a predetermined threshold level (i.e., under normal movement such as 5 p.s.i.) and prevents the release of air when pressure is applied above a predetermined load (under a high impact load i.e., 15 p.s.i.) based on the support's 10 application.

The ends 36A, 36B of the collar 12 have a connection device 38 that attaches the ends 36A, 36B of the collar 12 to fit about a user's neck. The connection device is of any type such as Velcro®, snaps, ties, buckles or the like and preferably is capable of breaking away in adverse situations such as when the collar 12 catches on an object during an accident.

In one embodiment, the sectional walls 20 have a conduit 40 that provides air ventilation to the interior sidewall 16 of the collar 12. Alternatively the conduits 40 are closed and filled with a cooling gel or fluid.

In operation, the collar 12 is placed around a user's neck and the ends 36A, 36B are connected using the connection device 38. Under normal conditions the user has a full range of neck and head movement. The full range of movement occurs because under small loads (i.e. approximately 5 p.s.i.) the affected cells 24 collapse as air is released through the check valve 28.

Under a higher impact load (i.e., 15 p.s.i.) the brace 10 provides support to the neck because the affected cells do not collapse. The cells do not collapse because the check valves prevent air from escaping from the cell 24 through port 26 at a predetermined level. In the preferred embodiment, under higher impact, air is forced toward port 26 such that the diaphragm moves to seal port 26 and prevent the release of air.

In an alternative embodiment, the neck support 10 has a cover 40 having a bottom 42, an inner wall 44, an outer wall 46, end walls 47 and a top wall 48 that form an enclosure 50. The inner wall 44 has at least one, and preferably, a plurality of openings or ports 52. Attached over the ports 52 is a porous material 54 such as a mesh or the like to filter air flow. Preferably, the porous material 54 is sewn to the inner wall 44 on the inside of the enclosure 50. The outer wall 46 also has at least one and preferably a plurality of openings or ports 56 with a porous material 58 that covers the openings 56. Preferably, the porous material 58 is sewn to the outer wall 46 on the inside of the enclosure 50. Mounted about the openings 58 are air ducts 68 that are positioned and formed to direct flowing air into openings 58. A cover (not shown) may be placed over the air duct 68 or a filter (not shown) placed within the air duct 68 to restrict the flow of dust and the like into opening 58.

A closure device 62, such as a zipper or the like permits access into the enclosure. While the closure device 62 is positioned at any convenient location on the cover 40, preferably it is positioned at the edge between the top wall 48 or the bottom wall 42 and the outer wall 46 to allow for maximum signage.

Inserted into the enclosure 50 is a support member 64. The support member 64 may be of one-piece construction with a top portion and bottom portion or multiple pieces. Preferably, the support member 64 has three sections, namely a first top section 66 and a second middle section 68 and a third bottom section 70. The support member 64 preferably is made of foam. Disposed within the support member are outer and inner openings (72 and 74) that are connected by conduits 76. In one example, the first top section 66 has two outer openings 72 that align with openings 58 on the outer wall 46 of the cover 40. The top section 66 also has an exhaust opening 78 that is in alignment with an exhaust opening 80 disposed on the outer wall 46 of the cover 40. The first section 66 also has a pair of openings 74 that are in alignment with openings 52 on the inner wall of the cover 40.

The second middle section 66 has a plurality of openings 84 that are in alignment with openings 52 on the inner wall 44 of the cover 40. These openings 84 are also in vertical communication with openings 72. Extending from openings 84 are conduits or channels 76 that extend to and are in communication with openings 74. Finally, second section 66 has a rear inner opening 88 that is in vertical communication with exhaust opening 78. Rear inner opening 88 also has a pair of conduits 90 that extend to and are in communication with openings 74.

A closure strap 92 is removably attached to the outer wall 46 across ends walls 47 in any conventional manner an preferably with a hook and loop Velcro® system. The closure strap has a surface where indicia such as a product label may be printed. Also, patches 94 are attached to outer wall 46. The patches 94 have a surface where indicia may be printed.

In operation, once support member 64 is inserted into enclosure 50 of the cover 40, the closure device 62 is closed and the neck support 10 placed around an individual's neck. The neck support 10 is held in place by securing the closure strap 92 to the outer wall 46 of the cover.

As the individual moves, such as when in motion on a motorcycle, air flows into air ducts 68 and then openings 72. Once in openings 72 some air will flow into openings 84 and onto a user's neck. Some of the air in opening 84 will travel down conduits 76 and exit through exhaust openings 78 and 80, and some will exit through opening 74 to the user's neck. Finally, the air around the user's neck will flow to rear inner opening 88 and exit through openings 78 and 80. In this manner, a support has been shown that protects against injury and also cools the user while wearing.

Thus a neck support has been disclosed that, at the very least, meets all of the stated objectives.

It will be appreciated by those skilled in the art that other various modifications could be made to the device without the parting from the spirit and scope of this invention. All such modifications and changes fall within the scope of the claims and are intended to be covered thereby.

What is claimed is:

1. A neck support comprising:
   a cover having at least one opening on each of an inner wall and an outer wall;
   a support member disposed within the cover and having an outer opening in alignment with the opening on the outer wall of the cover, an inner opening in alignment with the opening of the inner wall of the cover, and a conduit in communication with the inner and outer opening of the support member; and
   a porous material positioned to cover the opening on the inner wall.

2. The support of claim 1 wherein the support member is made of foam.

3. The support of claim 1 wherein the support member comprises more than one section.

4. The support of claim 1 wherein an air duct is attached to the outer wall in alignment with the opening on the outer wall.

5. The support of claim 1 wherein the neck support has an arcuate shape.

6. The support of claim 1 wherein the neck support extends in an arcuate fashion around a user's neck.

7. The support of claim 1 wherein the neck support takes the shape of a discontinuous hollow cylinder.

8. The support of claim 1 wherein air flows through the openings in the cover and the support member and onto a user's neck.

9. A neck support comprising:
   a cover having at least one opening on each of an inner wall and an outer wall;
   a support member disposed within the cover and having an outer opening in alignment with the opening on the outer wall of the cover, an inner opening in alignment with the opening of the inner wall of the cover, and a conduit in communication with the inner and outer opening of the support member; and
   an air duct attached to the outer wall in alignment with the opening on the outer wall.

10. The support of claim 9 wherein the support member is made of foam.

11. The support of claim 9 wherein the support member comprises more than one section.

12. The support of claim 9 further comprising a porous material positioned to cover the opening on the inner wall.

13. The support of claim 9 wherein the neck support has an arcuate shape.

14. The support of claim 9 wherein the neck support extends in an arcuate fashion around a user's neck.

15. The support of claim 9 wherein the neck support takes the shape of a discontinuous hollow cylinder.

16. The support of claim 9 wherein air flows through the openings in the cover and the support member and onto a user's neck.

17. A neck support comprising:
    a cover having at least one opening on each of an inner wall and an outer wall;
    a support member disposed within the cover and having an outer opening in alignment with the opening on the outer wall of the cover, an inner opening in alignment with the opening of the inner wall of the cover, and a conduit in communication with the inner and outer opening of the support member; and
    wherein air flows through the openings in the cover and the support member and onto a user's neck.

18. The support of claim 17 wherein the support member is made of foam.

19. The support of claim 17 wherein the support member comprises more than one section.

* * * * *